United States Patent [19]

Eberhard et al.

[11] Patent Number: 5,278,884
[45] Date of Patent: Jan. 11, 1994

[54] COMPLETE 3D CT DATA ACQUISITION USING PRACTICAL SCANNING PATHS ON THE SURFACE OF A SPHERE

[75] Inventors: Jeffrey W. Eberhard; Kristina H. V. Hedengren, both of Schenectady, N.Y.

[73] Assignee: General Electric Company, Schenectady, N.Y.

[21] Appl. No.: 992,672

[22] Filed: Dec. 18, 1992

[51] Int. Cl.$^5$ .......................... A61B 6/00; G06F 15/42
[52] U.S. Cl. ........................................ 378/4; 378/15; 378/901; 364/413.13; 364/413.15; 250/363.02
[58] Field of Search ...................... 378/4, 10, 15, 901, 378/19; 364/413.15, 413.14, 413.19, 413.13; 250/363.02; 358/111

[56] References Cited

U.S. PATENT DOCUMENTS

| | | | |
|---|---|---|---|
| 4,752,691 | 6/1988 | Hawman | 378/10 |
| 4,942,596 | 7/1990 | Eberhard et al. | 378/109 |
| 5,023,895 | 6/1991 | McCroskey et al. | 378/4 |
| 5,068,882 | 11/1991 | Eberhard | 378/4 |
| 5,073,910 | 12/1991 | Eberhard et al. | 378/4 |
| 5,170,439 | 12/1992 | Zeng et al. | 378/901 |
| 5,187,659 | 2/1993 | Eberhard et al. | 364/413.15 |

OTHER PUBLICATIONS

"Quantitative Cone-Beam reconstruction", Hui Hu et al., SPIE vol. 1092 Medical Imaging III: Image Processing (1989), pp. 492-501.
"The Dynamic Spatial Reconstructor", Robb et al., Journal of Medical Systems, vol. 4, No. 2, 1980, pp. 253-288.
"Practical Cone-Beam Algorithm", Feldkamp et al., J. Opt. Soc. Am. A/Vol. 1, No. 6, Jun. 1984, pp. 612-619.
"Convolutional Reconstruction From Cone-Beam Projection Data", G. N. Minerbo, IEEE Transaction on Nuclear Science, vol. NS-26, No. 2, Apr. 1979, pp. 2682-2684.
"An Inversion Formula for Cone-Beam Reconstruction", H. K. Tuy, Siam J. Appl. Math., vol. 43, No. 3, Jun. 1983, pp. 545-552.
"Image Reconstruction from Cone-Beam Projections: Necessary and Sufficient Conditions and Reconstruction Methods", Bruce D. Smith, IEEE Transactions on Medical Imaging, vol. MI-4, No. 1, Mar. 1985, pp. 14-25.
"Iterative Three-Dimensional Reconstruction from Twin-Cone Beam Projections", M. Schlindwein, IEEE Transactions on Nuclear Science, vol. NS-25, No. 5, Oct. 1978, pp. 1135-1143.
"Algebraic Reconstruction Techniques (ART) for Three-Dimensional Electron Microscopy and X-Ray Photography", Gordon et al., J. Theor. Biol. (1970) 29, pp. 471-481.
"Tomographic Reconstruction from Experimentally Obtained Cone-Beam Projections", Webb et al., IEEE Transactions on Medical Imaging, vol. M1-6, No. 1, Mar. 1987, pp. 67-73.
"Cone-Beam Tomography: Recent Advances and a Tutorial Review", Bruce D. Smith, Optical Engineering, May 1990, vol. 29, No. 5, pp. 524-534.
"Analysis of a 3D Imaging System by Reconstruction from X Radiographies in Conical Geometry", Pierre Grangeat, Doctoral Thesis, pp. 1-303.

Primary Examiner—David P. Porta
Assistant Examiner—Kim-Kwok Chu
Attorney, Agent, or Firm—Paul R. Webb, II

[57] ABSTRACT

Complete CT data acquisition is provided by scanning path trajectories located on a sphere or approximately located on a sphere. The scanning path trajectories are at least bounded between two relatively close spheres. The various scanning paths include sinusoids, square waves, circles, and arcs.

20 Claims, 5 Drawing Sheets

COMPLETE 3D CT DATA ACQUISITION USING PRACTICAL SCANNING PATHS ON THE SURFACE OF A SPHERE

BACKGROUND OF THE INVENTION

The present invention relates to three-dimensional (3D) computerized tomography (CT) and, more particularly, methods and systems providing complete data scanning paths on the surface of a sphere.

In conventional computerized tomography for both medical and industrial applications, an x-ray fan beam and a linear array detector are employed. Two-dimensional (2D) imaging is achieved. While the data set is complete and image quality is correspondingly high, only a single slice of an object is imaged at a time. When a 3D image is required, a stack of slices approach is employed. Acquiring a 3D data set one 2D slice at a time is inherently slow. Moreover, in medical applications, motion artifacts occur because adjacent slices are not imaged simultaneously. Also, dose utilization is less than optimal, because the distance between slices is typically less than the x-ray collimator aperture, resulting in a double exposure to many parts of the body.

In 2D CT, the scanning path of the source is often a simple circular scan about the object. The linear array detector is fixed relative to the source. (Although it is usual to talk about a scan path of a source relative to the object to be imaged, it is to be appreciated that the object may be rotated or otherwise moved to provide relative motion between the object and the source.)

To avoid the slowness of the 2D stack of slices approach for 3D imaging, some systems employ true cone beam geometry for 3D imaging. In such systems, a cone beam x-ray source and a 2D area detector are used. An object is scanned, preferably over a 360° angular range, either by moving the x-ray source in a scanning circle around the object or by rotating the object while the source remains stationary. In either case, the area detector is fixed relative to the source. The relative movement between the source and object which is to be imaged provides scanning in either case. Compared to the 2D stack of slices approach to achieve 3D imaging, the cone beam geometry has the potential to achieve rapid 3D imaging of both medical and industrial objects with improved dose utilization.

The standard scanning path used in cone beam 3D CT imaging is a single circle scan of source and detector around the object. However, the data acquired in a single scanning circle can be shown to be incomplete for 3D CT imaging.

Complete data scanning paths are known for 3D CT, but they often provide complete data at the expense of implementation complexity or impracticality. For example, two perpendicular circle scans around the object to be imaged provide complete data, but such scans cannot be readily implemented on standard computerized numerical controllers (CNC). U.S. Pat. No. 5,073,910 issued Dec. 17, 1991 to the present inventors discloses a complete data scanning path. Further, U.S. patent application Ser. No. 07/992,673, filed on concurrently herewith, in the name of one of the present inventors, Jeffrey W. Eberhard, discloses various complete data cone beam 3D scanning paths. The patent application and the patent, both of which are assigned to the assignee of the present application, are hereby incorporated by reference. No representation is being made that the subject matter of the patent application and patent are necessarily prior art to the present application. (Moreover, it is expressly noted that U.S. patent application Ser. No. 07/992,673, docket, discloses one embodiment of the present invention in connection with its description of techniques for setting sampling intervals or steps in various data scanning paths.)

The criteria for data set completeness relative to scanning path in a 3D CT system are described in the paper by Bruce D. Smith entitled "Image Reconstruction From Cone-Beam Projections: Necessary and Sufficient Conditions and Reconstruction Methods", IEEE Transactions on Medical Imaging, Volume MI-4, No. 1, pages 14-25 (March 1985), hereby incorporated by reference.

The above-mentioned Eberhard et al. U.S. Pat. No. 5,073,910 patent discloses, among other things, complete data scanning paths on the surface of a cylinder. Although such data scanning paths are generally quite useful, it would also be helpful to have further complete data scanning paths. Moreover, there is a lack of uniformity of Radon space filling in connection with the scanning paths on the surface of a cylinder. Such cylindrical scanning paths require a relatively large number of steps to calculate the Radon transform of the cone beam data set.

OBJECTS AND SUMMARY OF THE INVENTION

Accordingly, it is a primary object of the present invention to provide scanning path trajectories for use in 3D CT imaging.

A more specific object of the present invention is to provide such scan path trajectories which are relatively simple to implement.

A further object of the present invention is to provide scan path trajectories which are practical for implementation with standard computerized numerical controllers.

A still further object of the present invention is to provide scan path trajectories which provide complete 3D CT data acquisition.

Yet another object of the present invention is to provide scan path trajectories having uniformity of Radon space filling and a reduction in the number of steps required to calculate the Radon transform of the cone beam data set.

The above and other objects and advantages of the present invention which will become more apparent from the detailed description below are realized by a scanning and data acquisition method for three-dimensional computerized tomography imaging of a field of view containing at least a portion of an object. Imaging energy is applied from a source to the portion of the object. The source is moved relative to the object (i.e., this includes moving the object relative to the source) in a non-planar scanning trajectory (i.e., the trajectory is not confined to a single plane) located on the surface of a three-dimensional shape enclosing the portion of the object. The shape is bounded between an inner sphere of radius $r-L$ and an outer sphere of radius $r+L$, where r is a radius of an intermediate sphere between the inner and outer spheres, L is a positive constant which is no more than 10% of r, the inner, intermediate, and outer spheres are all concentric and centered at point C, and wherein orthogonal x, y, and z axes have their origin at point c and any point on the trajectory has an angle $\Theta$ within an xy plane relative to the x axis and an angle $\phi$ representing the azimuthal angle between the point on the trajectory and the z axis, and wherein $\phi$ is limited to more than 170° and no less than 10°. Data is acquired by use of an area detector to detect imaging energy which is passed through the portion of the object. A CT image is displayed based on the acquire data.

More specifically, L is less than 5% of r. Even more specifically, L is less than 1% or r.

In a first series of embodiments of the present invention, the trajectory is located completely on the intermediate sphere such that any point on the trajectory is a distance of r from the point C. Among a first embodiment within this set, the trajectory is a two cycle sinusoid on the intermediate sphere. More specifically, the two cycle sinusoid is centered about the xy plane. A second embodiment within this first set of embodiments uses a trajectory which is a two cycle square wave on the intermediate sphere, the two cycle square wave being centered about the xy plane. A third embodiment uses a trajectory which is a circle combined with a tilt arc defining an arc plane, the arc plane being preferably perpendicular to a plane in which the circle is disposed. The fourth embodiment within this first set of embodiments uses a trajectory which is two parallel circles connected by two arcs.

As an alternative to the various embodiments wherein the trajectory is located completely on the intermediate sphere, the trajectory is a plurality of lines disposed on planar tiles disposed between the inner and outer spheres, each planar tile extending over a range of no more than 5° relative to $\Theta$ and a range of no more than 5° relative to $\phi$.

In its more specific aspects, $\phi$ is no more than 160° and no less than 20°. More specifically, $\phi$ is no more than 150° and no less than 30°. Even more specifically, $\phi$ is no more than 135° and no less than 45°.

The three-dimensional computerized tomography system according to the present invention includes a source of imaging energy for applying imaging energy to at least a portion of an object to be imaged. A two-dimensional area detector is positioned to receive imaging energy from the source. A scanning means causes relative motion of the source and the object such that the source moves along a scanning trajectory relative to the object. A trajectory defining means operatively connected to the scanning means causes the scanning means to provide a trajectory of the types described above. A display is operatively connected to the area detector for displaying a CT image based on imaging energy received by the area detector.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
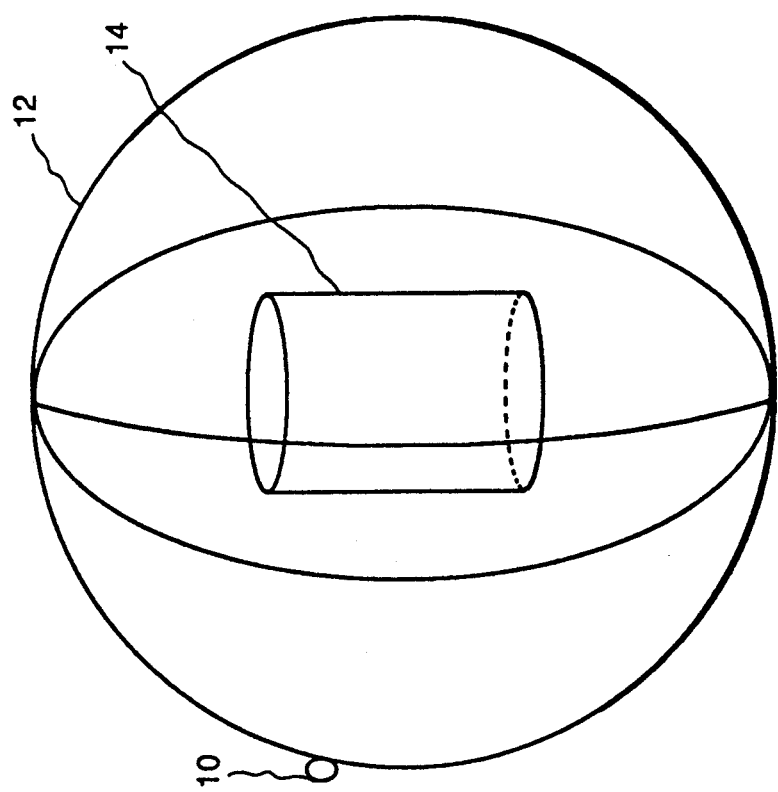
FIG. 1 shows a simplified perspective view illustrating a principle of the present invention.

FIG. 1 shows the general scanning configuration used by the present invention. In particular, a source 10, illustrated schematically, will be moved along a spherical scanning surface 12 relative to an object 14 which is to be imaged. More precisely, 14 is an object portion which is to be imaged. In other words, 14 may be part of other structures, but 14 is the portion of the workpiece which is to be imaged. More generally, it will be understood that the object 14 is not necessarily a workpiece or a portion thereof, but may be a human or animal patient or portion thereof which is to be imaged for medical purposes. Whether the object 14 is part of a workpiece being analyzed for industrial purposes, or a portion of a human or animal patient being analyzed for medical purposes, the frame of reference which will generally be used in this discussion will be the frame of reference of the object 14. Thus, the discussion will refer to the trajectory or scan path of source 10. However, it will be understood that the relative motion between source 10 and object 14 may be accomplished by moving source 10 while object 14 is stationary, moving object 14 while source 10 is stationary, or by moving both the object 14 and source 10 at the same time. In medical applications where the object 14 is a patient or part of a patient, the source 10 is usually moved while the patient is stationary. In industrial applications where the object 14 is part of all of a workpiece, the workpiece is usually moved while the source 10 is maintained stationary.

It should be emphasized that in FIG. 1 the particular scanning path trajectory is not illustrated. Instead, FIG. 1 simply shows several lines to define a sphere 12. According to one aspect of the present invention, the source 10 will be moved along the surface of sphere 12. Since the scan path trajectory will be specified such that every plane passing through the object 14 (portion of workpiece or patient which is to be viewed) passes through the source path at least once, the data set will be complete under criteria previously described in, for example, the 1985 publication of Smith incorporated by reference above. Significantly, the data scan paths will provide for complete cone beam data with minimal manipulator complexity and with no re-fixturing or re-gripping of the part (assuming that 14 is a workpiece or other industrial part) during the scan.

As will be generally appreciated in this field, a 2D area detector (not shown in FIG. 1) would be used in conjunction with the source 10. Specifically, the area detector would detect imaging energy which has passed through the object 14. Usually, and as contemplated by the present invention, the area detector would be fixed relative to the source 10. In other words, the detector would move relative to the object 14, but would not move relative to the source 10. However, the present invention does not necessarily require that the area detector is fixed relative to the source 10.

The source 10 is preferably an x-ray source, but could alternately be a source of neutrons, positrons, or other form of radiation or electromagnetic energy from a point source. Alternately, other forms of imaging energy might be used.

Figure 2:
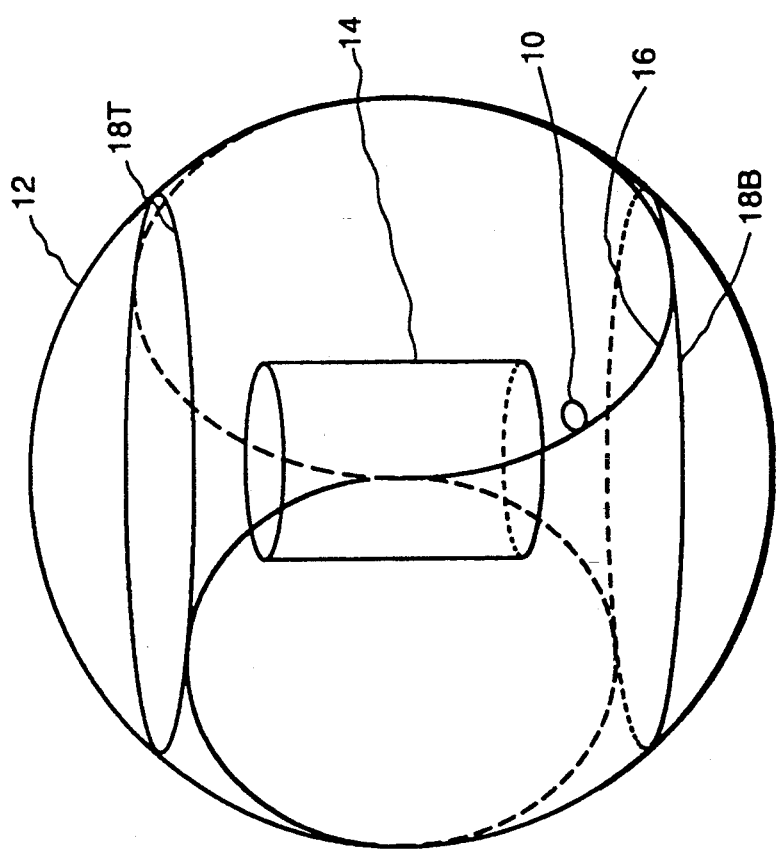
FIG. 2 shows a first embodiment of the present invention.

Turning now to FIG. 2, a first embodiment scanning path trajectory 16 is shown. Specifically, the trajectory 16 is a two cycle sinusoid located on the surface of the sphere 12 and centered about an xy plane (not shown in FIG. 2, will be discussed below) which is parallel to and centered between the end faces of the cylindrical object 14. (Note that object 14 is simply shown as a cylinder, but may of course have various other shapes.) The sinusoid 16 is disposed between an upper circle 18T located on sphere 12 and a lower circle 18B located on sphere 12.

Figure 7:
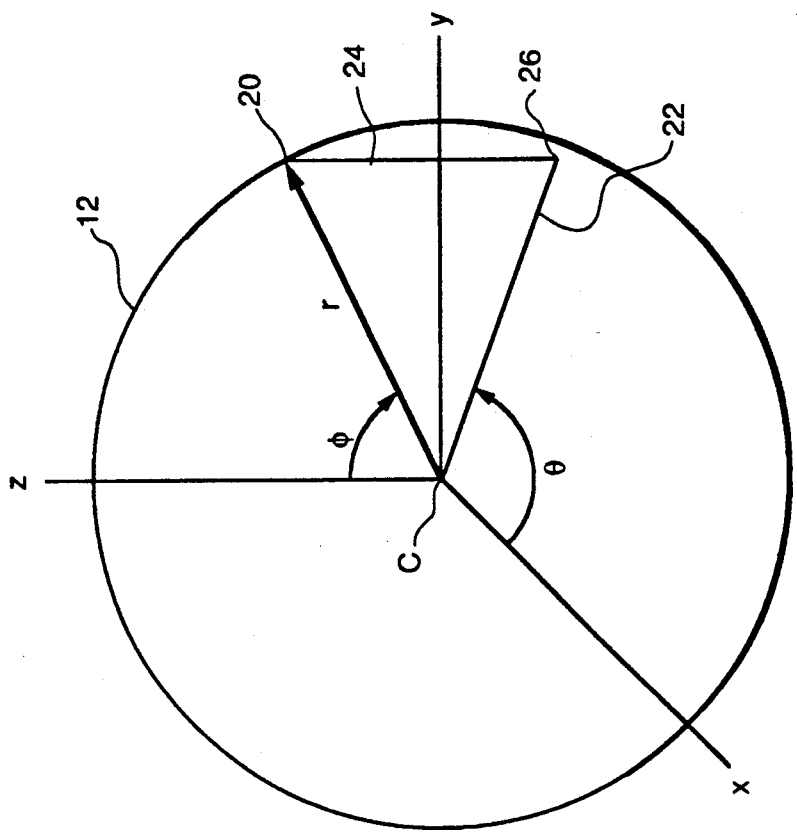
FIG. 7 shows the spherical coordinates as used with the present invention.

In order to better describe the scan path trajectory 16 of FIG. 2, it may be useful to briefly refer to FIG. 7 illustrating commonly used spherical coordinates. For a point 20 located on a sphere 12 of radius r, the point 20 is defined by $\Theta$ and $\phi$. $\Theta$ and $\phi$ are defined relative to orthogonal x, y, and z axes having their origin coincident with point C, the center of the sphere 12. In particular, the $\Theta$ of point 20 is the illustrated angle between line 22 corresponding to the projection of the line between point C and point 20 into the xy plane and the positive side of the x axis. The projection 22 is of course obtained by simply drawing a line 24 parallel to the z axis to locate a point 26 where the line intersects the xy plane. The angle $\phi$ is the illustrated angle between the positive z axis and the radius extending between origin C and point 20. Referring back to FIG. 2, the trajectory 16 would be defined by the following equations:

$$x = r\cos\Theta(1 - \tfrac{3}{4}\cdot\sin^2 2\Theta)^{\frac{1}{2}}$$

$$y = r\sin\Theta(1 - \tfrac{3}{4}\cdot\sin^2 2\Theta)^{\frac{1}{2}}$$

$$z = r/(3)^{\frac{1}{2}} \sin 2\Theta$$

Figure 3:
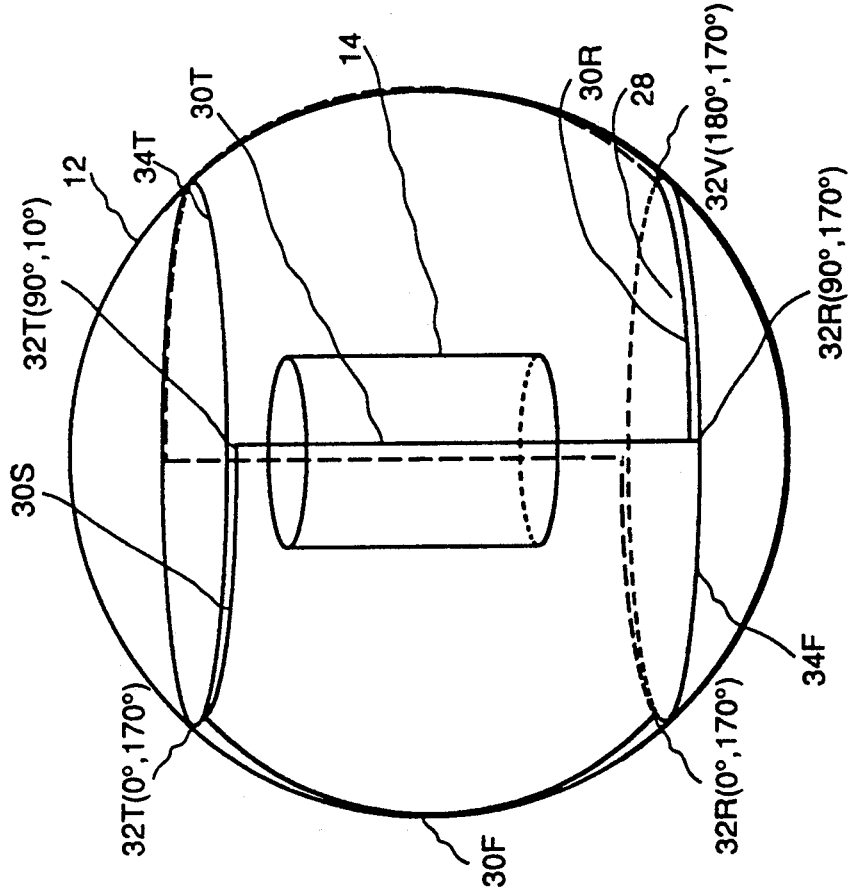
FIG. 3 shows a scan path trajectory for a second embodiment of the present invention.

Turning now to FIG. 3, a second embodiment of the present invention uses a trajectory 28 which is a two cycle square wave on the sphere. More specifically, the trajectory 28 includes a series of segments. A first segment 30F corresponds to $\Theta = 0$ and $\phi$ extends from, for example, 170° to 10°. Thus, the segment 30F is an arc on the sphere 12 extending between a first point 32F corresponding to $\Theta$ of 0° and $\phi$ of 170° and a second point 32S having a $\Theta$ of 0° and $\phi$ of 10°. From arc 30F, the trajectory 28 leads to arc 30S which extends from point 32S to point 32T corresponding to a $\Theta$ of 90° and $\phi$ of 170°. The trajectory 28 includes a fourth segment or arc 30R extending from point 32R to a point 32V having a $\Theta$ of 180° and $\phi$ of 170°. The four arcs 30F, 30S, 30T, and 30R define one cycle of the two cycle square wave and it will be readily understood that the other cycle may be defined in the same fashion. Generally, the trajectory 28 is bounded by a top circle 34T and a bottom circle 34B, both of the circles being parallel to the xy plane and the end faces of cylindrical object 14 in the illustrated view. For ease of illustration, the points 32F, 32S, and 32V have been shown slightly offset from the sphere 12.

Figure 4:
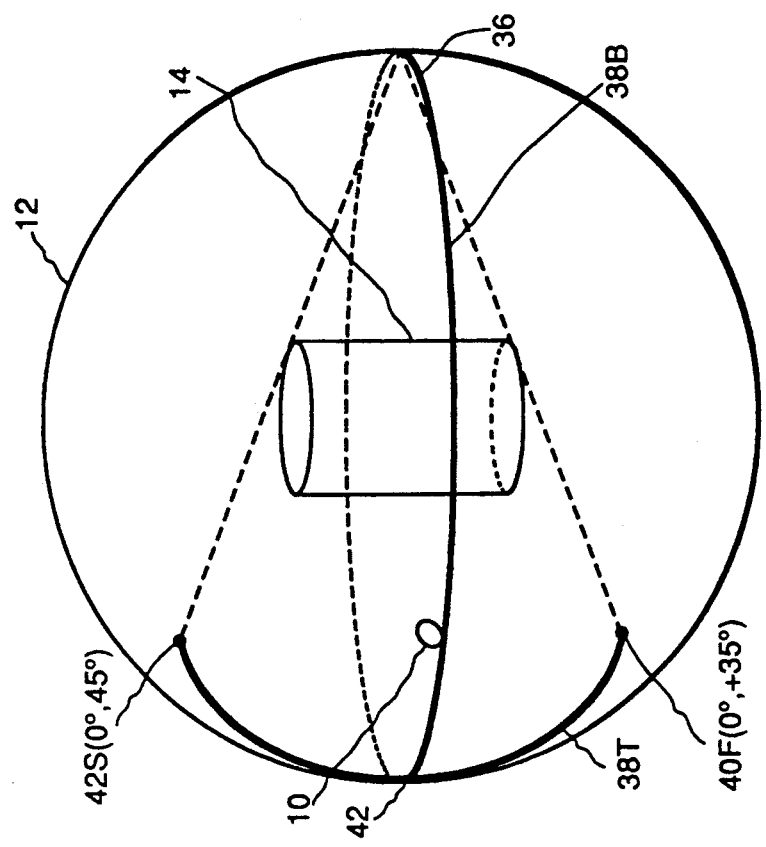
FIG. 4 shows a scan path trajectory for a third embodiment of the present invention.

Turning now to FIG. 4, a trajectory 36 has the source 10 moving in a circle 32C, which would be parallel to the xy plane (plane not illustrated in FIG. 4, but it is parallel and centered between end faces of cylindrical object 14). The circle 38C corresponds to a $\Theta$ running between 0° and 360° and a $\phi$ of 90°. Additionally, the trajectory 36 includes a tilt arc 38T extending between point 40F having a $\Theta$ of 0° and $\phi$ of 135° and second point 40S having a $\Theta$ of 0° and $\phi$ of 45°. As with the range of $\phi$ in the example of FIG. 3, the values for $\phi$ in FIG. 4 could be different from those given. For ease of illustration, the points 40F and 40S having been shown somewhat offset from the edge of the sphere 12, but it is emphasized that all of the trajectory 36 will be located on the sphere 12. When the source 10 travels along circle 38C and reaches the intersection 42 between the circle 38C and tilt arc 38T, the source 10 will scan down to point 40F and back up to point 40S before returning to point 42 and scanning further along the circle 38. the source 10 could alternately move from point 42 to 40S before moving down to point 40F.

Figure 5:
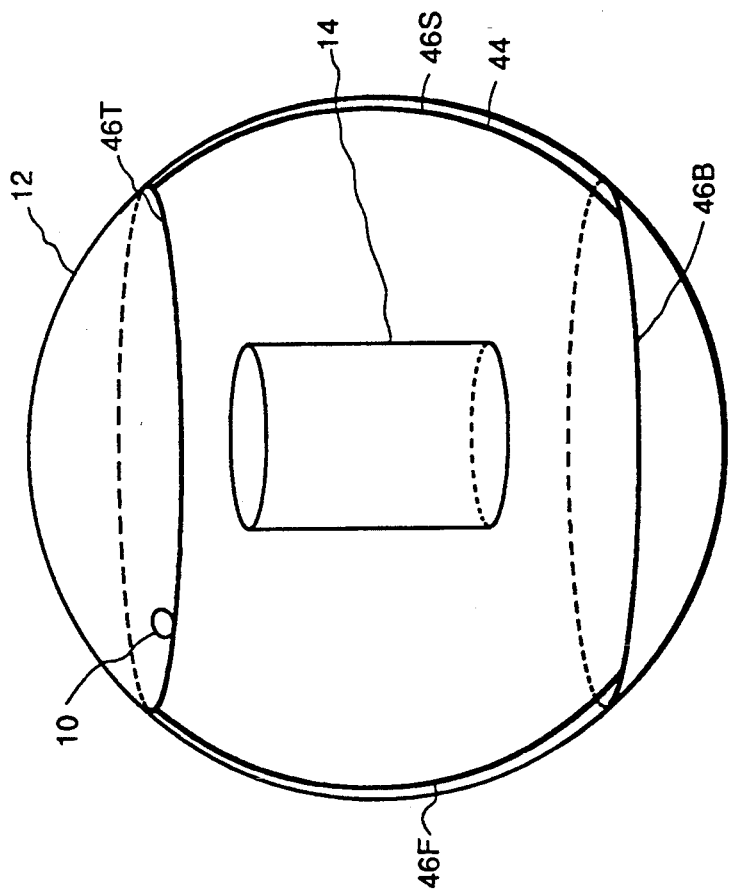
FIG. 5 shows a scan path trajectory for a fourth embodiment of the present invention.

Turning now to FIG. 5, a trajectory 44 according to a fourth embodiment of the present invention is illustrated. The source 10 moves along different portions of the trajectory 44 including a top circle 46T, a bottom circle 46B parallel to the top circle and first and second tilt arcs 46F and 46S (which are offset from each other by 180°. Various patterns could be used to scan all the portions of trajectory 44. For example, the source 10 could scan 360° around top circle 46T, then move down tilt arc 46F, scan one and a half times (540°) around bottom circle 46B before moving up second tilt arc 46S in order to scan the upper circle 46T again. Other patterns could of course be used.

Provided that the sphere and trajectory on the sphere are properly chosen, each of the above embodiments will provide a complete data set for 3D cone beam imaging. In addition, since the scanning occurs on the surface of a sphere, the line between the source and the origin of Radon space is always perpendicular to the detector plane. This simplifies the calculation of the Radon transform from the cone beam data in two ways. First, no pre-interpolation is required to achieve this favorable configuration (in contrast to the case for scans on the surfaces of a cylinder). Second, the interpolation coefficients required in the calculation of focal beam projections are simple and re-useable from line to line in the data set for this geometry.

Figure 6:
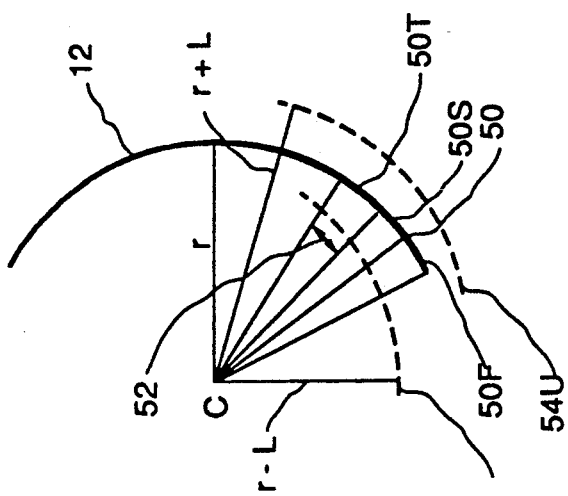
FIG. 6 shows a planar view of several spheres to illustrate a fifth embodiment scan path trajectory according to the present invention and to illustrate a general principle of other embodiments of the present invention.

Turning now to FIG. 6, a further embodiment trajectory according to the present invention will be discussed. The trajectory is not separately shown as such in FIG. 6, but will be understood to be disposed upon a polyhedral 50 which approximates the sphere 12 (only partially shown). For illustrative purposes, FIG. 6 has shown the sphere 12 mated to the polyhedral 50. For ease of illustration, only three tiles or sections 50F, 50S, and 50T have been shown, but it will be understood that the polyhedral 50 may extend sufficiently close to the sphere 12 to approximate the sphere 12 over at least a portion of the sphere 12 to allow a trajectory to be disposed upon the polyhedral 50 in order to provide complete data for 3D CT cone beam scanning. Each of the tiles 50F, 50S, 50T, and similar tiles not illustrated would extend about an angular range 52 which extends no more than 5° relative to $\Theta$ and extends no more than 5° relative to $\phi$.

Whether the trajectory is disposed upon a polyhedral such as 50 of FIG. 6 in order to approximate a sphere 12 or is disposed upon an actual sphere 12 as in the previous embodiments, it will be appreciated that the trajectory will be disposed upon a three dimensional shape which is bound between an inner sphere 54N and an outer sphere 54U. The inner sphere 54N has a radius of r−L, whereas the outer sphere 54U has a radius of r+L, where L is a positive constant less than 10% of r. More specifically, L is less than 5% of r. Even more specifically, L is less than 1% of r. It will be appreciated that in the previously discussed embodiments of FIGS. 2-5, L is effectively 0. At any rate, all of those embodiments as well as the embodiment described specifically with reference to FIG. 6 have scan path trajectories which are limited to between the inner sphere 54N and the outer sphere 54U.

Figure 8:
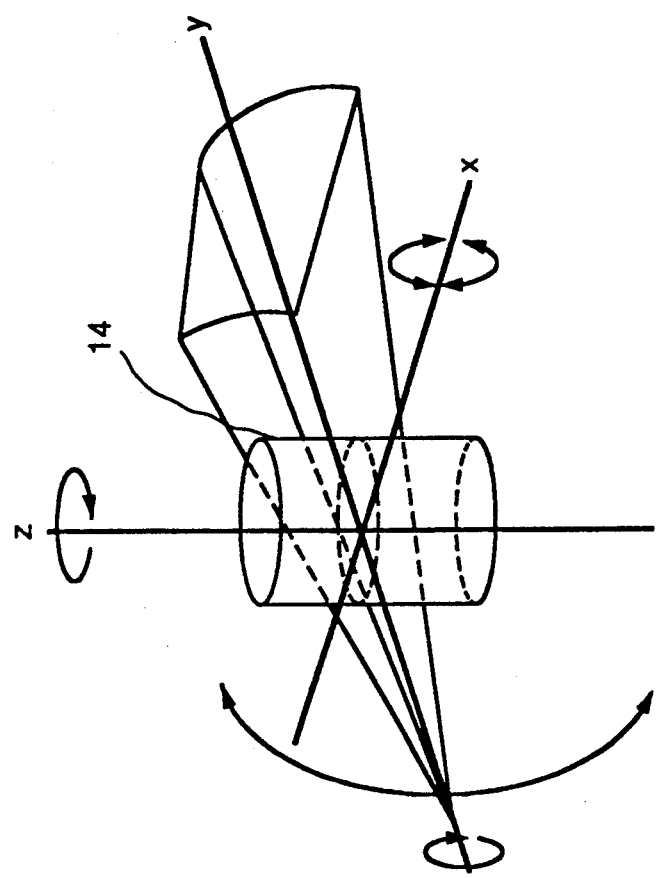
FIG. 8 is a simplified perspective demonstrating various degrees of freedom which may be used by a computerized numerical controller to obtain the scanning path trajectories according to the present invention.

Scanning patterns other than those specifically mentioned may be implemented with multiple tilt axes such as illustrated schematically with respect to the object 14 in FIG. 8. The various degrees of freedom illustrated schematically in FIG. 8 may be used in numerical controllers having these degrees of freedom would, more specifically, be used, although simpler computerized numerical controllers might also be used. Various combinations of rotation axes, tilt axes, and translation axes could be used for implementing the present invention. Although not specifically illustrated, scanning patterns including ramps, saw tooths, and other analytic or discrete sampling patterns could also be used for the present invention. Although cylindrical shaped field of view regions (i.e., the object 14 in the various figures) are shown in the figures, other shapes for the object field of view such as spherical or irregular polyhedral shapes which fit within the scanning surface might also be used.

It should be understood that the present invention may use scanning which is either step-wise or continuous motion. Data would be acquired at a set of discrete points along the path and the intervals between data acquisition points in the path may be determined by reference to the incorporated by reference U.S. patent application Ser. No. 07/992,673.

Figure 9:
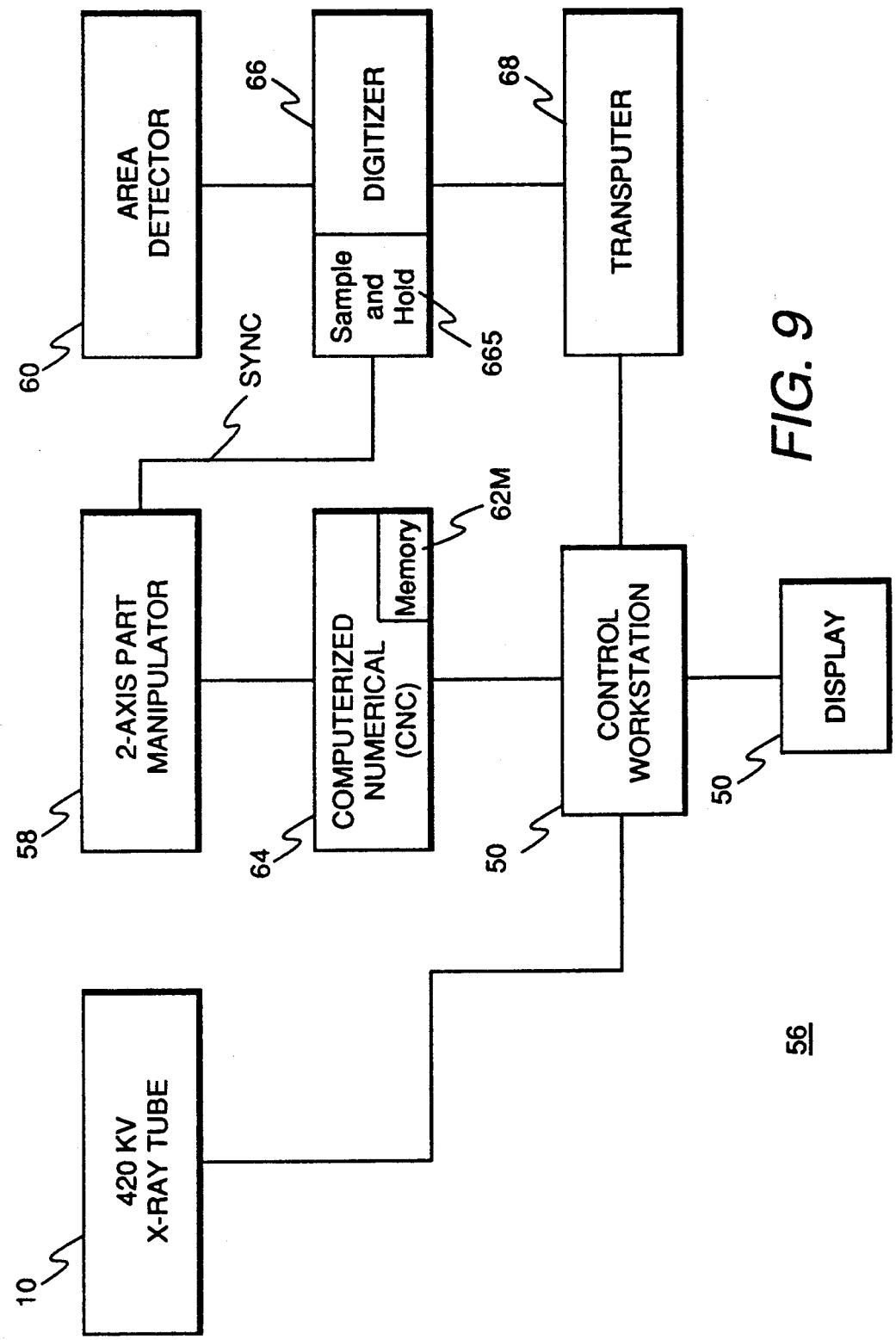
FIG. 9 is a simplified block diagram illustrating the components of the present invention.

With reference now to FIG. 9, the system 56 according to the present invention will be discussed. The source 10 applies imaging energy to an object (not shown in FIG. 9) under control of manipulator 58, which may be a two axis part manipulator as shown. The manipulator 58 serves as a scanning means for moving the object 14 (shown only in the previous figures) in order to provide the scanning trajectories as discussed. It will be readily appreciated that the scanning means could alternately be an arrangement for moving the source 10 as previously discussed. The imaging energy from source 10 is detected by an area detector 60. The various components within the system 56 are controlled by a computer work station 62 having a memory 62N. The computer work station 62 controls the manipulator 58 by way of a computerized numerical controller 64 which may include a memory portion 64M. Programs stored within one or both of the memories 62M and 64M cause one or both of the memories to serve as a trajectory defining means to use the manipulator 58 to provide a trajectory of the type discussed above with respect to the figures of the present application.

A digitizer 66 receives analog signals from the area detector 60 and converts them into digital form. A synch signal is supplied to sample and hold circuits 66S within the digitizer 66 in order to cause the digitizer 66 to acquire data at a particular time. The synch signal is shown as being provided by manipulator 58, but could be provided by other components. The digital signals from digitizer 66 are supplied to a transputer 68 which may be of a known commercially available type such as Meiko M40. The transputer 68 is an array processor which provides the necessary signal processing for the signals coming from the digitizer 66. A display 70 displays a CT image based on data provided either directly by the transputer 68 (not shown) or, as illustrated, based upon data supplied to the display 70 by way of the computer work station 62.

Although various specific constructions have ben given for the present invention, it is to be understood that these are for illustrative purposes only. Various modifications and adaptations will be readily apparent to those of skill in the art. For example, although the present invention has been described with reference to source which physically moves relative to the object during the scanning operation, an alternative is possible. In such an alternative, a material may be around or partially around the object to be viewed which material generates imaging energy upon being struck by a different kind of energy beam. The beam applied to the source material causes the source material to in turn emit an imaging energy. Although the source is not physically moved relative to the object, the source would effectively be moved relative to the object by sweeping the beam striking the source material in a path corresponding to the trajectory. In similar fashion and as used herein, moving the source relative to the object shall include situations where a series of sources are turned on sequentially to effectively move the source as well as the beam striking a source material type of source movement. In view of these and other modifications, the scope of the present invention should be determined by reference to the claims appended hereto.

What is claimed is:

1. A scanning and data acquisition method for three-dimensional computerized tomography (CT) imaging of a field of view containing at least a portion of an object, the method comprising the steps of:

applying imaging energy from a source to said portion of said object;

moving the source relative to the object in a nonplanar scanning trajectory located on the surface of a three-dimensional geometrically defined spherical shape, said portion of the object to be imaged being substantially centered within said spherical shape;

said shape being bounded between an inner sphere of radius r−L and an outer sphere of radius r+L, where r is a radius of an intermediate sphere between the inner and outer spheres, L is a positive constant which is no more than 10% of r, the inner, intermediate, and outer spheres are all concentric and centered at point C, and where orthogonal x, y, and z axes have their origin at point C and any point on the trajectory has an angle $\Theta$ within an xy plane relative to the x axis and an angle $\phi$ representing the azimuthal angle between the point on the trajectory and the z axis, and wherein $\phi$ is limited to no more than 170° and no less than 10°;

acquiring data by using an area detector to detect imaging energy which is passed through said portion of the object; and displaying a CT image based on the acquire data.

2. The method of claim 1 wherein L is less than 5% of r.

3. The method of claim 2 wherein L is less than 1% of r.

4. The method of claim 1 wherein the trajectory is located completely on the intermediate sphere such that any point on the trajectory is a distance of r from the point C.

5. The method of claim 4 wherein the trajectory is a two cycle sinusoid on the intermediate sphere.

6. The method of claim 5 wherein the two cycle sinusoid is centered about the xy plane.

7. The method of claim 4 wherein the trajectory is a two cycle square wave on the intermediate sphere.

8. The method of claim 7 wherein the two cycle square wave is centered about the xy plane.

9. The method of claim 4 wherein the trajectory is a circle combined with a tilt arc defining an arc plane.

10. The method of claim 9 wherein the arc plane is perpendicular to a plane in which the circle is disposed.

11. The method of claim 4 wherein the trajectory is two parallel circles connected to by arcs.

12. The method of claim 1 wherein the trajectory is a plurality of lines disposed on planar tiles disposed between the inner and outer spheres, each planar tile extending over a range of no more than 5° relative to $\Theta$ and a range of no more than 5° relative to $\Theta$.

13. The method of claim 1 wherein $\phi$ is no more than 160° and no less than 20°.

14. The method of claim 13 wherein $\phi$ is no more than 150° and no less than 30°.

15. The three-dimensional computerized tomography (CT) system comprising:
   a source of imaging energy for applying imaging energy to at least a portion of an object to be imaged;
   a two-dimensional area detector positioned to receive imaging energy from the source;
   a scanning means causing relative motion of the source and the object such that the source moves along a scanning trajectory relative to the object;
   trajectory defining means operatively connected to the scanning means to cause said scanning means to provide a trajectory located on the surface of a three-dimensional geometrically defined spherical shape, said portion of the object to be imaged being substantially centered within said spherical shape, said shape being bounded between an inner sphere of radius $r-L$ and an outer sphere of radius $r+L$, where r is a radius of an intermediate sphere between the inner and outer spheres, L is a positive constant which is no more than 10% of r, the inner, intermediate, and outer spheres are all concentric and centered at point C, and wherein orthogonal x, y, and z axes have their origin at point C and any point on the trajectory has an angle $\Theta$ within an xy plane relative to the x axis and an angle $\phi$ representing the azimuthal angle between the point on the trajectory and the x axis, and wherein $\phi$ is limited to no more than 170° and no less than 10°; and
   a display operatively connected to said area detector for displaying a CT image based on imaging energy received by said area detector.

16. The system of claim 15 wherein the trajectory is located completely on the intermediate sphere such that any point on the trajectory is a distance of r from the point C.

17. The system of claim 15 wherein the trajectory is a two cycle sinusoid on the intermediate sphere.

18. The system of claim 15 wherein the trajectory is a two cycle square wave on the intermediate sphere.

19. The system of claim 15 wherein the trajectory is a circle combined with a tilt arc defining an arc plane.

20. The system of claim 15 wherein the trajectory is two parallel circles connected by two arcs.

* * * * *